United States Patent [19]

Parker et al.

[11] Patent Number: 5,208,347
[45] Date of Patent: May 4, 1993

[54] PROCESS FOR THE SYNTHESIS AND RECOVERY OF TETRAHYDRO-N-[1-METHYL-1-[3-(1-METHYLETHENYL)-PHENYL]ETHYL]-2-OXO-1-H-PYRROLO-1-CARBOXAMIDE

[75] Inventors: Dane K. Parker, Massillon; Richard T. Musleve, Akron, both of Ohio

[73] Assignee: The Goodyear Tire & Rubber Company, Akron, Ohio

[21] Appl. No.: 876,149

[22] Filed: Apr. 30, 1992

[51] Int. Cl.$^5$ .......................................... C07D 207/12
[52] U.S. Cl. .................................................. 548/538
[58] Field of Search ........................................ 548/538

[56] References Cited

U.S. PATENT DOCUMENTS 5,043,455  8/1991  Parker et al. ..................... 548/537

Primary Examiner—Joseph Paul Brust
Attorney, Agent, or Firm—Alvin T. Rockhill

[57] ABSTRACT

The present invention discloses a process for the preparation of tetrahydro-N-[1-methyl-1-[3-(1-methylethenyl)phenyl]ethyl]-2-oxo-1-H-pyrrolo-1-carboxamide which is comprised of (1) reacting m-isopropenyl α,α-dimethylbenzylisocyanate with 2-pyrrolidinone at a temperature which is within the range of about 80° C. to about 150° C. to produce a molten reaction product; (2) mixing the molten reaction product with an aqueous emulsifier solution to form an aqueous medium, wherein the aqueous emulsifier solution contains from about 0.1 weight percent to about 10 weight percent emulsifier, and wherein the weight ratio of the molten reaction product to the emulsifier solution in the aqueous medium is within the range of 1:0.5 to 1:100; (3) allowing the tetrahydro-N-[1-methyl-1-[3-(1-methylethenyl)phenyl]ethyl]-2-oxo-1-H-pyrrolo-1-carboxamide in the aqueous medium to crystallize under conditions of agitation into the form of essentially spherical particles; and (4) recovering the tetrahydro-N-[1-methyl-1-[3-(1-methylethenyl)phenyl]ethyl]-2-oxo-1-H-pyrrolo-1-carboxamide particles from the aqueous medium by filtration.

14 Claims, No Drawings

PROCESS FOR THE SYNTHESIS AND RECOVERY OF TETRAHYDRO-N-[1-METHYL-1-[3-(1-METHYLETHENYL)-PHENYL]ETHYL]-2-OXO-1-H-PYRROLO-1-CARBOXAMIDE

BACKGROUND OF THE INVENTION

Tetrahydro-N-[1-methyl-1-[3-(1-methylethenyl)-phenyl]ethyl]-2-oxo-1-H-pyrrolo-1-carboxamide (TOPC) has the structural formula:

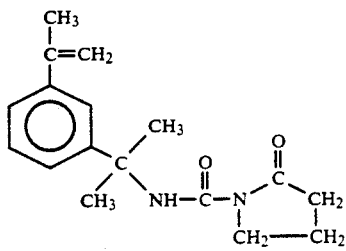

and is an excellent choice as a monomer having pendant blocked isocyanate groups which can be polymerized into rubbers. TOPC is a solid at room temperature and is readily soluble in most monomers commonly used in making synthetic rubber, such as styrene, acrylonitrile, 1,3-butadiene, isoprene, acrylates, vinylidene chloride, and the like. It will also readily polymerize by either solution or emulsion free radical means under a wide variety of conditions with varying initiator systems, such as azo compounds, peroxides, persulfates and redox systems. Additionally, TOPC will not retard normal polymerization rates.

Rubbers having pendant blocked isocyanate groups which are made with TOPC do not deblock at temperatures below about 160° C. This is highly desirable since deblocking at low temperatures can result in premature crosslinking (scorch) during coagulation, drying and/or compounding steps. Rubbers made with TOPC can also be coagulated by utilizing standard procedures.

Rubbers which are made utilizing TOPC as a comonomer have units which are derived from TOPC incorporated therein. These repeat units which are derived from TOPC have the following structure:

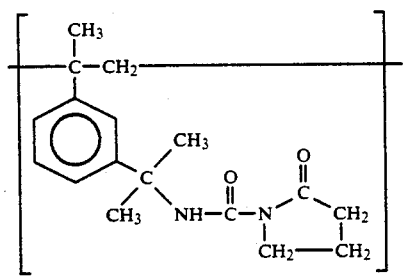

and can be distributed throughout the polymer chains of the rubber in an essentially random manner. Such rubbers will also typically contain repeat units which are derived from conjugated diene monomers, such as isoprene or 1,3-butadiene and can be deblocked by simply heating to temperatures above about 160° C. The deblocking reaction is very fast at temperatures within the range of about 180° C. to about 200° C. As a result of the deblocking reaction, repeat units having the structural formula:

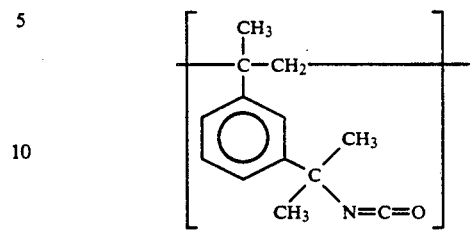

which contain unblocked isocyanate groups are formed and 2-pyrrolidinone (2-pyrrolidone) is liberated. The 2-pyrrolidinone is believed to be relatively non-toxic and has a boiling point of 245° C.

U.S. Pat. No. 5,043,455 discloses that TOPC monomer can be synthesized by the reaction of TMI with 2-pyrrolidinone at a temperature within the range of about 80° C. to 150° C. In this reaction one mole of TMI reacts with one mole of 2-pyrrolidinone to produce one mole of TOPC. U.S. Pat. No. 5,043,455 indicates that the reaction product formed can be mixed into an aliphatic liquid hydrocarbon, such as hexane, pentane or octane, to induce crystallization of the TOPC. Unfortunately, there are environmental and safety problems associated with the use of such liquid organic compounds in inducing the crystallization of the TOPC.

SUMMARY OF THE INVENTION

This invention is based upon the unexpected discovery that aqueous emulsifier solutions can be used to induce the crystallization of TOPC. By utilizing the techniques of this invention, the need to use liquid organic compounds to induce the crystallization of TOPC is eliminated. Additionally, the TOPC which is recovered when the techniques of this invention are employed is in the form of dense, non-dusting discreet particles which are essentially spherical in form. Such particles can be easily recovered by filtration and are in a convenient form for further handling.

The subject invention more specifically reveals a process for the preparation of tetrahydro-N-[1-methyl-1-[3-(1-methylethenyl)phenyl]ethyl -2-oxo-1-H-pyrrolo-1-carboxamide which is comprised of (1) reacting m-isopropenyl α,α-dimethylbenzylisocyanate with 2-pyrrolidinone at a temperature which is within the range of about 80° C. to about 150° C. to produce a molten reaction product; (2) mixing the molten reaction product with an aqueous emulsifier solution to form an aqueous medium, wherein the aqueous emulsifier solution contains from about 0.1 weight percent to about 10 weight percent emulsifier, and wherein the weight ratio of the molten reaction product to the emulsifier solution in the aqueous medium is within the range of 1:0.5 to 1:100; (3) allowing the tetrahydro-N-[1-methyl-1-[3-(1-methylethenyl phenyl]ethyl]-2-oxo-1-H-pyrrolo-1-carboxamide in the aqueous medium to crystallize under conditions of agitation into the form of essentially spherical particles; and (4) recovering the tetrahydro-N-[1-methyl-1-[3-(1-methylethenyl)phenyl]ethyl]-2-oxo-1-H-pyrrolo-1-carboxamide particles from the aqueous medium by filtration.

DETAILED DESCRIPTION OF THE INVENTION

In the first step of the process of this invention, m-isopropenyl α,α-dimethylbenzylisocyanate, which is also known as 1-(1-isocyanato-1-methylethyl)-3-(1-methylethenyl)-benzene or TMI, is reacted with 2-pyrrolidinone. This reaction can be carried out over a very wide temperature range with temperatures between about 80° C. and about 150° C. being typical. It is generally preferred for this reaction to be conducted at a temperature within the range of 90° C. to 120° C. with temperatures in the range of 95° C. to 110° C. being most preferred. This reaction can be carried out in the absence of solvent and catalyst. However, the reaction can be catalyzed with dibutyltin dilaurate, alkyltin mercaptides, salts of bismuth, salts of lead, and the like.

In this reaction, one mole of TMI reacts with one mole of 2-pyrrolidinone to produce one mole of TOPC. It is normally preferred for a slight excess of 2-pyrrolidinone to be utilized in the reaction. For example, it is generally advantageous to employ the 2-pyrrolidinone in an excess of about 2 mole percent to about 5 mole percent. Larger excesses of 2-pyrrolidinone in this reaction slows the crystallization of TOPC.

A listing of various emulsifiers which may be useful in this invention is given in the book "McCutcheon's Emulsifiers and Detergents 1981 Annuals", which is incorporated herein by reference in its entirety. The emulsifiers useful in this invention may be a combination of one or more emulsifiers of the anionic, cationic, non-ionic or amphoteric class of surfactants. Suitable anionic emulsifying agents are alkyl sulfonate, alkyl aryl sulfonates, condensed naphthalene sulfonate, alkyl sulfates, ethoxylated sulfates, phosphate esters, and esters of sulfosuccinic acid. Representative of these emulsifiers are sodium alpha-olefin ($C_{14}$–$C_{16}$) sulfonates, alkali metal or ammonium dodecylbenzene sulfonates, disodium dodecyl diphenyloxide disulfonate, disodium palmityl diphenyloxide disulfonate, sodium, potassium, or ammonium linear alkyl benzene sulfonate, sodium lauryl sulfate, ammonium alkyl phenolethoxylate sulfate, ammonium or sodium lauryl ether sulfate, ammonium alkyl ether sulfate, sodium alkyl ether sulfate, sodium dihexyl sulfosuccinate, sodium dicyclohexylsulfosuccinate, sodium diamyl sulfosuccinate, sodium diisobutylsulfosuccinate, disodium ethoxylated nonyl phenol half ester of sulfosuccinic acid, tetrasodium N-(1,2-dicarboxyethyl)-N-octadecyl sulfosuccinamate, disodium isodecyl sulfosuccinate, sodium bistridecyl sulfosuccinate, sodium salt of alkyl aryl polyether sulfate, lauryl alcohol ether sulfate, sodium salt of condensed napthalene sulfonic acid, complex phosphate ester of ethylene oxide adduct.

The aqueous emulsifier solution will normally contain from about 0.1 weight percent to about 10 weight percent of the emulsifier. It is normally preferred for the aqueous emulsifier solution to contain from 0.5 weight percent to 5 weight percent emulsifier with it being more preferred for the aqueous emulsifier solution to contain from 1 weight percent to 2.5 weight percent of the emulsifier.

The weight ratio of the molten reaction product to the aqueous emulsifier solution mixed in this step will normally be within the ratio of 1:0.5 to 1:100. It is normally preferred for the weight ratio of the molten reaction product to the aqueous emulsifier solution to be within the range of 1:0.7 to 1:10. It is generally most preferred for the ratio of molten reaction product to aqueous emulsifier solution to be within the range of 1:0.9 to 1:3.

In the second step of the process of this invention, the molten reaction product produced in the first step is mixed with an aqueous emulsifier solution. This can be done by adding the molten reaction product to the aqueous emulsifier solution or it can be accomplished by adding the aqueous emulsifier solution to the molten reaction product. In many cases, it will be desirable to conduct both the reaction and the crystallization in the same vessel. In such cases, the aqueous emulsifier solution will be added to the molten reaction product.

This mixing of the molten reaction product with the aqueous emulsifier solution is normally conducted under conditions of vigorous agitation. It is normally preferred for the molten reaction product to be cooled to a temperature within the range of about 40° C. to about 70° C. before it is mixed with the aqueous emulsifier solution. This facilitates a faster rate of crystallization.

The aqueous medium formed by mixing the molten reaction product and the aqueous emulsifier solution is then allowed to cool. As the aqueous medium cools, fine droplets of the liquid reaction product which are stabilized by the emulsifier in the mixture begin to crystallize into particles or beads which are essentially spherical in form. It is important to maintain the aqueous medium under conditions of agitation until the crystallization is complete to insure that an essentially spherical particulate product is formed. As this crystallization occurs, heat is given off. This heat of crystallization causes the temperature of the aqueous medium to increase to a measurable degree. By monitoring the temperature of the aqueous medium, the point at which crystallization is occurring can be detected by this increase in temperature. In the third step of the process of this invention, the TOPC is simply allowed to crystallize into discreet particles.

After the TOPC has crystallized, it is recovered in the fourth step of the process of this invention by filtration. The TOPC beads which are formed can be recovered by simply passing the aqueous medium containing such TOPC particles through a screen having a mesh size which is small enough to prevent them from passing through it. In most cases, a 100 mesh screen will be adequate for this purpose.

It may be desirable to wash the TOPC beads which are recovered with pure water. The beads can then, of course, be dried using any of a variety of standard drying procedures. For instance, the TOPC beads can be dried in warm dry air or under vacuum. The drying of TOPC will normally be done at a temperature of less than about 45° C. since TOPC has a melting range of about 52° C. to 55° C.

The following examples are merely for the purpose of illustration and are not to be regarded as limiting the scope of the invention or the manner in which it can be practiced. Unless specifically indicated otherwise, parts and percentages are given by weight.

EXAMPLE

A two liter, three-neck flask equipped with a large magnetic stir bar, condenser, dropping funnel, thermometer and nitrogen inlet tube was charged with 342.57 grams (4.025 moles) of 2-pyrrolidinone and 100 grams (0.497 moles) of distilled meta-TMI. The mixture was heated under nitrogen to a temperature of 100° C.

where a slight exotherm was noted (CA. 4° C.). At this point, an additional 704 grams of distilled meta-TMI (3.5 moles) was added with gel warming at a rate sufficient to maintain a reaction temperature of approximately 100° C. The mixture was allowed to react at this temperature for 23 hours. The reaction progress was periodically monitored by infrared analysis following the disappearance of the isocyanate absorption at 2255 cm$^{-1}$.

Then 300 grams of the reaction product was added to a one liter beaker at 65° C. Then 300 grams of an aqueous emulsifier solution containing 1 percent of a mixed fatty acid potassium soap was added to the molten reaction product in the beaker. The aqueous medium formed was vigorously agitated to form a uniform dispersion. After the aqueous medium had cooled to about 25° C., crystallization began. The heat given off by crystallization caused the temperature of the aqueous medium to increase to about 33° C. As soon as the temperature began to fall again, the agitation was stopped and the aqueous medium was filtered through a 100 mesh screen. White spherical particulate beads were recovered on the screen. They were subsequently washed with 1,200 ml of water and air dried. The beads which were recovered weighed 294 grams which represents a yield of 99.8 percent. Accordingly, this example shows that by utilizing the techniques of this invention, that TOPC can be synthesized and recovered at extremely high yields.

While certain representative embodiments and details have been shown for the purpose of illustrating the subject invention, it will be apparent to those skilled in this art that various changes and modifications can be made therein without departing from the scope of the subject invention.

What is claimed is:

1. A process for the preparation of tetrahydro-N-[1-methyl-1-[3-(1-methylethenyl)phenyl]ethyl]-2-oxo-1-H-pyrrolo-1-carboxamide which is comprised of (1) reacting m-isopropenyl α,α-dimethylbenzylisocyanate with 2-pyrrolidinone at a temperature which is within the range of about 80° C. to about 150° C. to produce a molten reaction product; (2) mixing the molten reaction product with an aqueous emulsifier solution to form an aqueous medium, wherein the aqueous emulsifier solution contains from about 0.1 weight percent to about 10 weight percent emulsifier, and wherein the weight ratio of the molten reaction product to the emulsifier solution in the aqueous medium is within the range of 1:0.5 to 1:100; (3) allowing the tetrahydro-N-[1-methyl-1-[3-(1-methylethenyl)phenyl]ethyl]-2-oxo-1-H-pyrrolo-1-carboxamide in the aqueous medium to crystallize under conditions of agitation into the form of essentially spherical particles; and (4) recovering the tetrahydro-N-[1-methyl-1-[3-(1-methylethenyl)phenyl]ethyl]-2-oxo-1-H-pyrrolo-1-carboxamide particles from the aqueous medium by filtration.

2. A process as specified in claim 1 wherein the aqueous emulsifier solution contains from about 0.5 weight percent to about 5 weight percent emulsifier.

3. A process as specified in claim 2 wherein the weight ratio of the molten reaction product to the emulsifier solution in the aqueous medium is within the range of 1:0.7 to 1:10.

4. A process as specified in claim 3 wherein the molten reaction mixture is cooled to a temperature within the range of about 40° C. to about 70° C. before it is mixed with the aqueous emulsifier solution.

5. A process as specified in claim 4 which further comprises washing the particles recovered from the aqueous medium with water.

6. A process as specified in claim 4 which further comprises drying the particles recovered from the aqueous medium.

7. A process as specified in claim 5 which further comprises drying the particles after they have been washed.

8. A process as specified in claim 6 wherein the weight ratio of the molten reaction product to the emulsifier solution in the aqueous medium is within the range of 1:0.9 to 1:3.

9. A process as specified in claim 8 wherein the aqueous emulsifier solution contains from 1 weight percent to 2.5 weight percent emulsifier.

10. A process as specified in claim 3 wherein the reaction of step (1) is carried out at a temperature within the range of 90° C. to 120° C.

11. A process as specified in claim 9 wherein the reaction of step (1) is carried out at a temperature which is within the range of 95° C. to 110° C.

12. A process as specified in claim 1 wherein the emulsifier is an anionic emulsifier.

13. A process as specified in claim 1 wherein the emulsifier is a cationic emulsifier.

14. A process as specified in claim 1 wherein the emulsifier is a nonionic emulsifier.

* * * * *